United States Patent [19]

Lura

[11] Patent Number: 5,351,522
[45] Date of Patent: Oct. 4, 1994

[54] GAS SENSOR

[75] Inventor: David B. Lura, Brooklyn Park, Minn.

[73] Assignee: Aequitron Medical, Inc., Minneapolis, Minn.

[21] Appl. No.: 147,326

[22] Filed: Nov. 2, 1993

[51] Int. Cl.⁵ .............................................. G01N 29/18
[52] U.S. Cl. ..................................... 73/24.01; 73/597
[58] Field of Search ................. 73/24.01, 64.53, 61.75, 73/61.79, 597, 861.18, 861.27, 861.28, 61.49

[56] References Cited

U.S. PATENT DOCUMENTS

| 4,144,752 | 3/1979 | Lolk | 73/861.28 |
| 5,060,506 | 10/1991 | Douglas | 73/24.01 |
| 5,060,514 | 10/1991 | Aylsworth | 73/24.01 |

FOREIGN PATENT DOCUMENTS 8303981  6/1984 Netherlands ............... 73/861.28

Primary Examiner—Hezron E. Williams
Assistant Examiner—Joseph W. Roskos
Attorney, Agent, or Firm—Palmatier, Sjoquist & Helget

[57] ABSTRACT

The invention relates to an oxygen sensor which measures the concentration of oxygen based upon ultrasonic sound waves traveling through a binary gas. The measured sound-wave delay through the gases determines the concentration level for oxygen within the transducer chamber. The invention includes an L-shaped housing where a transmitter/transducer is attached to one end of the housing and the receiver/transponder is positioned at the junction between the two substantially straight portions of the L-shaped housing. A straight transducer chamber is thereby provided, while simultaneously provided a housing design which minimizes reflected standing waves for detection by the receiver/transponder. The invention includes a sonic baffle positioned at the opposite end of the L-shaped housing from the transmitter/transducer which minimizes standing waves thereby improving the performance of the gas detection device. The invention also includes a sound buffer affixed to the interior of the L-shaped housing which further reduces the existence and reflection of standing waves for detection by the receiver/transponder. Temperature is monitored within the transducer chamber by an angularly offset temperature sensor.

46 Claims, 4 Drawing Sheets

GAS SENSOR

BACKGROUND OF THE INVENTION

This invention relates generally to an ultrasonic gas measuring device for detecting and determining the concentration of oxygen within a binary oxygen gas mixture. The concentration of oxygen within a binary gas mixture is then used in therapeutic medicinal applications. The invention incorporates a means for providing a more efficient and precise determination of the concentration of oxygen within a binary gas mixture, such as an oxygen/nitrogen mixture.

In the past, the analysis of simpler gas mixtures normally required the use of measurement techniques which involved difficult calibration procedures, replenishment of reagent chemicals, and/or other awkward, costly or time-consuming procedures.

Prior art devices have been developed to continuously monitor the ratio of two known gases within a gas mixture. A typical example of a binary gas composition to be measured would include oxygen/nitrogen mixtures used in the therapeutic administration of oxygen from oxygen concentrators in home health care environments. Additionally, respirators, ventilators, and air/oxygen blenders are commonly used in hospitals requiring known ranges of oxygen concentration. Gas concentration detection devices are also used in medical applications involving the application of anesthesia to individuals. In the medical field, many patients require supplemental oxygen. The two most common forms for the supply of oxygen include bottled oxygen compressed and confined within a canister, and oxygen concentrators which convert room air into oxygen. Many states require oxygen concentrators to include oxygen monitors installed to verify the concentration levels for the supply of therapeutic oxygen. Oxygen concentrator suppliers may therefore use oxygen monitors to verify correct operation, and reduce the need for maintenance of oxygen detection devices.

Prior art oxygen measurement devices are extremely sensitive to changes in temperature and are generally poorly temperature compensated. In addition, these devices are extremely sensitive to barometric pressure or humidity changes. Acoustical techniques have been used for gas analysis for measurement of the concentration of a particular gas within a binary gas mixture. The use of acoustical techniques creates severe technical problems with respect to the analysis of gases, due to the mechanical, electronic, and thermal problems associated with standing waves, temperature variations, and barometric pressure or humidity variances. The temperature of the gas must be measured and used to compensate for an accurate output reading. As the temperature increases, the sound waves within the transducer chamber travel at a faster rate due to the increased speed of the molecules of gas moving within the chamber.

Continuous wave systems have been considered appealing, due to the ability of such systems to use a resonant transmitter and receiver element which affords an adequate signal-to-noise ratio, acceptable sensitivity, and simplicity of design for a gas concentration measurement device. However, the continuous-wave approach is not free from problems, particularly with respect to standing waves within the closed transducer chamber. In a continuous-wave system, the receiver accepts acoustic energy from the transmitter within a transducer chamber and generates a signal, with a phase shift, which is affected by the mean molecular weight and temperature of the gas to be detected. The acoustical waves within the transducer chamber reflect from various surfaces, thus setting up standing waves that frustrate repeatability measurements. In addition, upon excitation of the transmitted energy, the receiver retransmits a signal at its anti-resonant frequency, in a complex fashion, back toward the transmitter. As a result, a beat frequency is encountered which yields unpredictable effects in response to temperature variations. The primary problem of gas-sensing devices, as known, is the standing waves which are encountered within the transducer chamber yielding unacceptable high signal-to-noise ratios and/or signal frequency errors.

The disclosed invention provides a more precise analysis of the concentration of a gas or gases within a gaseous mixture, primarily through the elimination of reflected standing waves within a transducer chamber. The invention thereby furnishes a more consistent and accurate analysis of the specific concentration of any one of the gases being detected, particularly oxygen, than can be achieved through the usage of the individual or combined prior art teachings.

An example of the prior art teachings include the U.S. Pat. No. 5,060,506 to Douglas and the U.S. Pat. No. 5,060,514 issued to Aylsworth. Both patents generally disclose ultrasonic gas measuring devices for the measurement of gas mixtures involving a transducer chamber having a design which does not minimize signal-to-noise ratios resulting from standing waves.

SUMMARY OF THE INVENTION

In general, the invention relates to an oxygen sensor which measures the concentration of oxygen based upon ultrasonic sound waves traveling through a binary gas. The measured sound wave delay through the gases determines the concentration level for oxygen within the transducer chamber. The invention includes an L-shaped housing where a transmitter/transducer is attached to one end of the housing and the receiver/transponder is positioned at the junction between the two substantially straight portions of the L-shaped housing. A straight transducer chamber is thereby provided, while simultaneously providing a housing design which minimizes reflected standing waves for detection by the receiver/transponder. Background noise is thereby significantly reduced while enhancing the signal-to-noise ratio for the gas detection device. The invention includes a sonic baffle positioned at the opposite end of the L-shaped housing from the transmitter/transducer which minimizes standing waves thereby improving the performance of the gas detection device. The invention also includes a sound buffer means affixed to the interior of the L-shaped housing which further reduces the existence and reflection of standing waves for detection by the receiver/transponder. Temperature is monitored within the transducer chamber by an angularly offset sensor which provides the necessary environmental conditions for the accurate determination of a gas concentration within the gas detection device.

It is an object of the present invention to provide a new and improved gas-sensor device of relatively simple and inexpensive design, construction, and operation which is accurate, safe, durable, and reliable, and which fulfills the intended purpose of measuring the concentration of oxygen within a binary gas mixture without fear of inaccurate readings, injury to persons, and/or damage to property.

It is another object of the present invention to reduce standing ultrasonic waves within a transducer chamber thereby improving the accuracy of the measured concentration of oxygen within the gas-sensor device.

It is still another object of the present invention to improve the signal-to-noise ratio within a transducer chamber thereby improving the accuracy of the measured concentration of oxygen within the gas-sensor device.

A feature of the present invention includes an L-shaped housing having a transmitter/transducer at one end, a sonic baffle at the opposite end of the L-shaped housing, and a receiver/transponder positioned approximately equal distances between the transmitter/transducer and the sonic baffle, where the L-shaped housing reduces standing waves for detection by the receiver/transponder.

Another feature of the present invention includes an angularly offset sensor for measuring the temperature of the gas within the transducer chamber for the provision of accurate environmental conditions for calculation of the concentration of oxygen within the gas-sensing device.

Still another feature of the present invention includes a conical-shaped sonic baffle having a plurality of longitudinal slots for reduction of standing waves within the L-shaped housing, thereby minimizing errors in the calculation of oxygen concentration within the transducer chamber.

Still another feature of the present invention includes a sound buffer means, formed of a sound-absorbent material, which is positioned proximal to the interior walls of the L-shaped housing minimizing standing waves within the transducer chamber.

DETAILED SPECIFICATION OF THE PREFERRED EMBODIMENT

Figure 1:
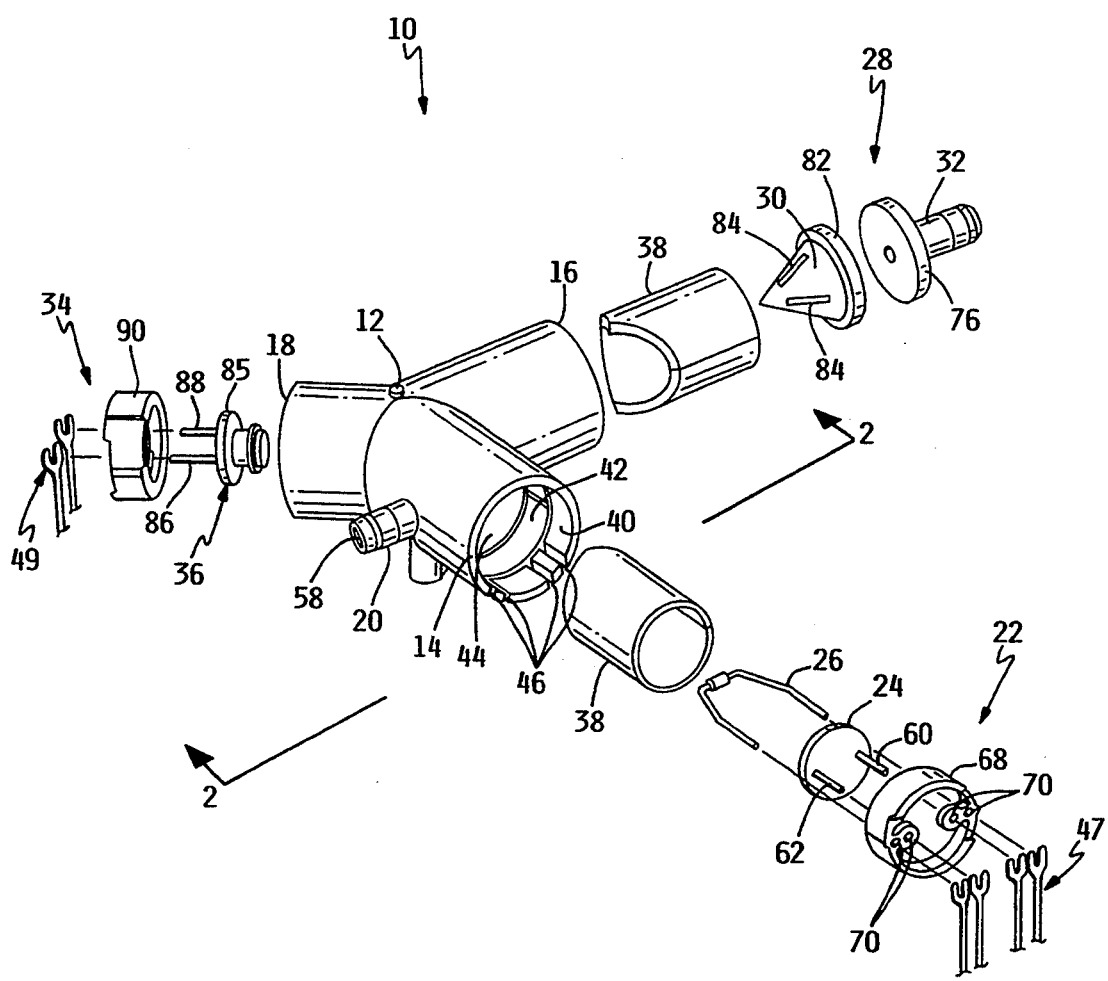
FIG. 1 is an exploded view of the invention.

One form of the gas-sensor device is illustrated and described herein. In general, the gas-sensor device is indicated by the numeral 10 and is used to detect the concentration of oxygen, based upon analysis of ultrasonic sound waves traveling through a binary gas sample. The sound-wave delay through the binary gas may be measured for calculation of the oxygen concentration level within a binary gas sample. An accurate determination of the concentration of oxygen requires analysis of various environmental conditions including, but not limited to, length of the chamber, temperature, pressure, and humidity. The gas-sensor device 10 is preferably used for analysis of a binary gas composed of a mixture of oxygen and nitrogen. As such, all components of the gas-sensor device 10 are preferably selected to be unaffected by, and/or non-reactive to, oxygen and nitrogen gas.

In general, the gas-sensor device 10 includes the following elements: an L-shaped housing 12 having a first transmitter end 14, a second gas outflow end 16, a junction open receiver end 18, and a gas inlet port 20; a transmitter assembly 22 having a transmitter/transducer 24, and a diode 26; a gas outflow cap assembly 28 having a sonic baffle 30, and a gas outlet port 32; a receiver assembly 34 having a receiver/transducer 36; and a sound buffer 38.

The L-shaped housing 12 is preferably of one-piece construction and is formed of injection-molded polycarbonate plastic material. Alternatively, the L-shaped housing 12 may be formed by bonding two pieces of polycarbonate material together proximal to the junction open receiver end 18. The L-shaped housing 12 is preferably formed to withstand internal gas pressure of twenty, plus or minus two pounds per square inch. The gas-sensor device 10 is preferably exposed to five pounds per square inch of pressure during normal operational conditions. In the event of a failure of an external pressure regulator, pressures in the range of twelve to fifteen pounds per square inch may be exposed to the L-shaped housing 12. The L-shaped housing 12 is preferably tubular, having a circular cross-sectional dimension. The L-shaped housing 12 preferably has an exterior diameter dimension approximating one inch and an interior diameter dimension approximating three-quarters of an inch. Within the interior of the L-shaped housing 12, a transducer chamber exists between the first open transmitter end 14 and the junction open receiver end 18. The transducer chamber is preferably linear, having a length dimension approximating one inch. A defined length for the transducer chamber optimizes the performance of the gas-sensor device 10, specifically with respect to the pulse width of the generated ultrasonic waves, over temperature and concentration conditions, within the L-shaped housing 12.

Generally, a linear transducer chamber maximizes performance of the gas-sensor device 10 during use of a pulsed sound wave. L-shaped housing 12 maximizes performance of the gas-sensor device 10 during use of sound waves which are continuously excited within the transducer chamber. An advantage of use of an L-shaped housing 12, during continuous sound-wave operation, is the reduction in the complication of electrical circuitry. Specifically, the delay and sample-and-hold circuitry are not required in continuous sound-wave operation, but are required in pulsed sound-wave operational conditions.

The L-shaped housing 12 includes a first open transmitter end 14, a second open gas outflow end 16, a junction open receiver end 18, and a gas inlet port 20. The first open transmitter end 14 and the second open gas outflow end 16 are preferably positioned at opposite ends of the L-shaped housing 12. The junction open receiver end 18 is preferably positioned equal distances from each of the first open transmitter end 14 and the second open gas outflow end 16. The gas inlet port 20 is preferably positioned equal distances between the first open transmitter end 14 and the junction open receiver end 18, passing through an exterior wall of the L-shaped housing 12.

The first open transmitter end 14 generally includes a first grooved surface 40, a second grooved surface 42, and a first interior surface 44. Second grooved surface 42 is preferably engaged to the transmitter assembly 22. The first grooved surface 40 is preferably positioned proximal, and encircles, the interior of the first open transmitter end 14. The first grooved surface 40 preferably has a diameter dimension slightly smaller than the exterior diameter dimension of the L-shaped housing 12. The second grooved surface 42 is preferably positioned proximal to the first grooved surface 40 encircling the interior of the L-shaped housing 12. The second grooved surface 42 is preferably of smaller diameter than the first grooved surface 40, facilitating engagement to the transmitter assembly 22. The first interior surface 44 is preferably positioned proximal to the second grooved surface 42 and extends the length of the transducer chamber within the interior of the L-shaped housing 12. The first interior surface 44 forms the interior diameter dimension of the L-shaped housing 12, which approximates three-quarters inch.

A plurality of engagement slots 46 traverse the first grooved surface 40. The engagement slots 46 are preferably adapted for coupling receipt of lead wires 47 which are electrically connected to electrical contacts of the transmitter/transducer 24.

The first open transmitter end 14 is adapted for receiving engagement of the transmitter assembly 22 within the interior of the L-shaped housing 12. The ledge created between the second grooved surface 42 and the first interior surface 44 preferably functions as a stop limiting the penetrating engagement of the transmitter assembly 22 within the first open transmitter end 14. The exact positioning of the transmitter assembly 22 is thereby accomplished by the precise formation of the width of the second grooved surface 42.

Figure 2:
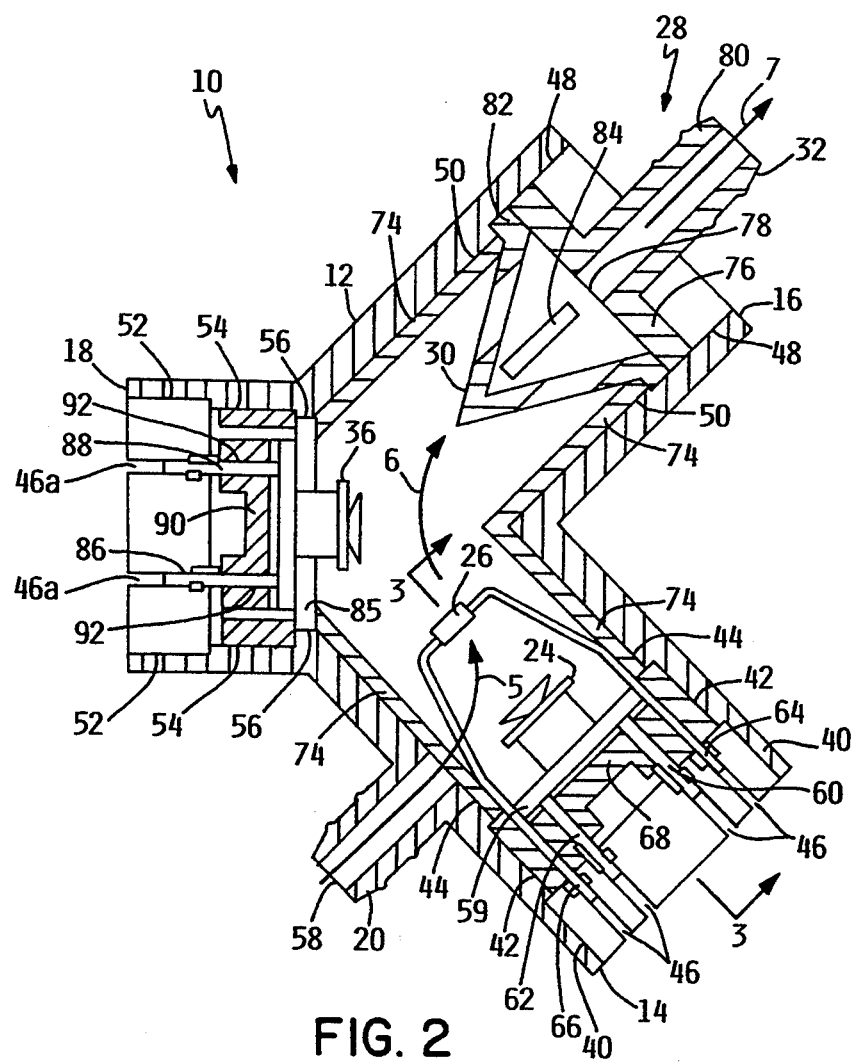
FIG. 2 is a cross sectional top view of the invention taken along a horizontal centerline.
Figure 3:
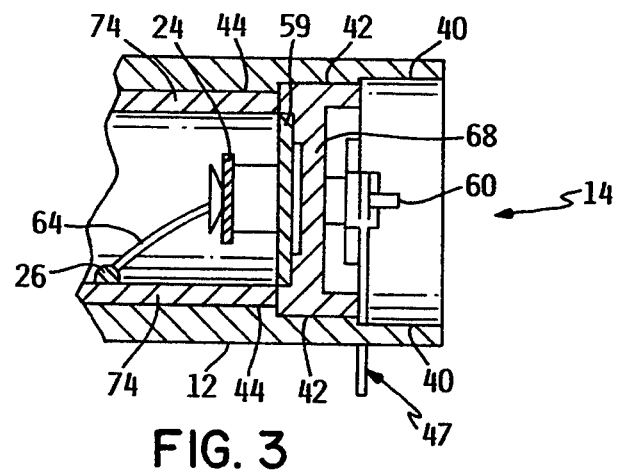
FIG. 3 is a cross sectional side view of the first transmitter end taken along the line 3—3 of FIG. 2.

Referring to FIG. 2, the open gas outflow end 16 generally includes a first channel surface 48 and a second interior surface 50. The first channel surface 48 is preferably engaged to the gas outflow end cap assembly 28. The first channel surface 48 is preferably positioned proximal to, and encircles, the interior edge of the second open gas outflow end 16. The first channel surface 48 preferably has a diameter dimension slightly smaller than the exterior diameter dimension of the L-shaped housing 12. The second interior surface 50 is preferably positioned proximal to the first channel surface 48 and extends the length of the L-shaped housing 12, between the second open gas outflow end 16 and the junction open receiver end 18. The second interior surface 50 forms the interior dimension of the L-shaped housing 12, which approximates three-quarters of an inch.

A portion of the circumference of the first channel surface 48 is preferably in flush engagement to the exterior surface of the gas outflow end cap assembly 28. The open gas outflow end 16 is thereby adapted for receiving engagement of the gas outflow end cap assembly 28 within the interior of the L-shaped housing 12. The ledge created between the first channel surface 48, and the second interior surface 50, preferably functions as a stop limiting the penetrating engagement of the gas outflow end cap assembly 28 within the second open gas outflow end 16. The exact positioning of the gas outflow end cap assembly 28 is thereby accomplished by the precise formation of the width of the first channel surface 48. The first channel surface 48 preferably has the same diameter dimension as the first grooved surface 40, and the second interior surface 50 preferably has the same diameter dimension as the first interior surface 44.

The junction open receiver end 18 generally includes a first ridge surface 52 and a second ridge surface 54. The second ridge surface 54 is preferably engaged to the receiver assembly 34. The first ridge surface 52 is preferably positioned proximal to, and encircles, the interior of the junction open receiver end 18. The first ridge surface 52 preferably has a diameter dimension slightly smaller than the exterior diameter dimension of the L-shaped housing 12. The second ridge surface 54 is preferably positioned proximal to the first ridge surface 52 encircling the interior of the L-shaped housing 12. The second ridge surface 54 is preferably of smaller diameter dimension than the first ridge surface 52, facilitating engagement to the receiver assembly 34.

A plurality of engagement slots 46a traverse the first ridge surface 52. The engagement slots 46a are preferably adapted for coupling receipt of lead wires 49 which are electrically connected to the electrical contacts of the receiver/transponder 36. Preferably, the entire circumference of the second ridge surface 54 is in flush engagement to the exterior surface of the receiver assembly 34. The junction open receiver end 18 is thereby adapted for receiving engagement of the receiver assembly 34 within the interior of the L-shaped housing 12. The exact positioning of the receiver assembly 34 is thereby accomplished by the precise formation of the width of the second ridge surface 54. The first ridge surface 52 preferably has the same diameter dimension as the first grooved surface 40 and the first channel surface 48; the second ridge surface 54 preferably has the same diameter dimension as the second grooved surface 42.

It should be noted that the diameter of the second ridge surface 54 has a smaller dimension than either the first interior surface 44 or the second interior surface 50. A stop ledge 56 is thereby established at the position of the interface between the second ridge surface 54 and the first interior surface 44 and the second interior surface 50. The stop ledge 56 functions to limit the penetration of the receiver assembly 34 into the junction open receiver end 18.

The gas inlet port 20 is preferably positioned equidistant between the first open transmitter end 14 and the junction open receiver end 18. The gas inlet port 20 includes a central aperture 58 and is preferably molded through the L-shaped housing 12. The central aperture 58 preferably passes through an exterior wall of the L-shaped housing 12 defining the inlet for the flow of binary gas to be analyzed by the gas-sensor device 10. It should be noted that the position of the gas inlet port 20 may be suitably relocated to any preferred position with respect to the L-shaped housing 12, so long as the binary gas inlet is positioned proximal to the transducer chamber. The gas inlet port 20 may be of any preferred length, width, and diameter dimensions at the discretion of an individual provided that the essential functions, features, and attributes described herein are not sacrificed.

The gas inlet port 20 is preferably formed of the same plastic material as the L-shaped housing 12 and is thereby able to withstand, without fracture or fail, gas pressure within the range of twenty pounds per square inch. Alternatively, a gas inlet port 20 may be attached to the L-shaped housing 12 by threaded penetrating and receiving means as may be available. If a threaded inlet port is to be used, a sealing means may additionally be required to insure the sealed integrity between the gas inlet port 20 and the L-shaped housing 12.

The gas inlet port 20 may include ribs at the preference of an individual to facilitate engagement to a hose connected in air-flow relation to a binary gas source.

In general, the transmitter assembly 22 includes a transmitter/transducer 24 mounted to a transmitter base 59, an electrical ground connection 60, and an electrical input connection 62; a diode 26 having an anode 64 and a cathode 66; and a transmitter end cap 68 having a plurality of apertures 70 (FIGS. 1 and 2).

The transmitter end cap 68 is preferably formed of the same polycarbonate or plastic material as the L-shaped housing 12. The transmitter end cap 68 is preferably cylindrical in shape having a diameter adapted for flush and sealed engagement to the second grooved surface 42 of the first open transmitter end 14. The width dimension of the transmitter end cap 68 is preferably equal to the width dimension of the second grooved surface 42. The transmitter end cap 68 includes a plurality of apertures 70 which are adapted for alignment to the engagement slots 46 of the first grooved surface 40. The apertures 70 provide for the convenient electrical connection of lead wires 47 to the electrical ground connection 60, electrical input connection 62, anode 64, and cathode 66.

The purpose of the transmitter end cap 68 is to seal the first open transmitter end 14, and centrally position the transmitter/transducer 24 within the interior of the L-shaped housing 12. Another purpose of the transmitter end cap 68 is to position the transmitter/transducer 24 at a fixed location with respect to the transducer chamber, such that a defined calculated distance dimension exists between transmitter/transducer 24 and the receiver/transponder 36. A known distance between the transmitter/transducer 24 and the receiver/transponder 36 enables an individual to calculate the time delay for the passing of ultrasonic waves through a binary gas, thereby enabling an individual to determine the concentration of a gas within a binary gas mixture.

The transmitter/transducer 24 is preferably mounted to a transmitter base 59 which is cylindrical in shape and is formed of the same plastic material as the transmitter end cap 68. The electrical ground connection 60 and the electrical input connection 62 preferably pass through the transmitter base 59 for the ultimate electrical connection to the lead wires 47. The electrical ground connection 60 and the electrical input connection 62 then pass through the central pair of apertures 70 of the transmitter end cap 68. It should be noted that the transmitter base 59 is preferably affixed to the transmitter end cap 68 and is positioned for flush engagement thereto. It should also be noted that the lead wires 47 are preferably positioned for electrical connection to the electrical ground connection 60 and the electrical input connection 62, and the anode and cathode connections.

The diode 26 preferably extends from the transmitter end cap 68 toward the receiver/transponder 36 a distance approximating 0.6 inches. The diode 26 includes connector wires which pass through the exterior pair of apertures 70, of the transmitter end cap 68, for connection to the lead wires 47. Diode 26 may be a Type IN4148, and the purpose of the diode 26 is to continuously monitor the temperature of the binary gas within the transducer chamber. The temperature of the binary gas, in addition to the distance between the transmitter and receiver elements, is required in order to calculate the concentration of a gas within the gas detection device 10.

The diode 26 is angularly offset with respect to the transducer chamber and the path existing between the transmitter/transducer 24 and the receiver/transponder 36. The diode 26 preferably does not interfere with the ultrasonic waves generated by the transmitter/transducer 26, to an extent requiring inclusion of a factor or term in a time delay equation during the calculation of the concentration of a gas within a binary gas mixture. The diode 26 preferably does not cause standing waves within the transducer chamber thereby interfering with the signals to be detected by the receiver/transponder 36 during use of the gas-sensor device 10. The diode 26 is preferably located at a substantially central position approximately equidistant between the transmitter/transducer 24 and the receiver/transponder 36. The diode 26 is also preferably positioned proximal to, but not in contact with, the sound buffer 74 within the interior of the L-shaped housing 12.

The transmitter end cap 68, electrical ground connection 60, electrical input connection 62, anode 64, and cathode 66 are preferably sealed within the first open transmitter end 14 by potting compound. It should be noted that the apertures 70 are preferably restricted or plugged following engagement to the electrical ground connection 60, electrical input connection 62, anode 64, and cathode 66, in order to facilitate sealing of the first open transmitter end 14. Following the curing of the potting compound for a period approximating twenty-four hours, a seal of the transmitter end cap 68 should occur where the seal is able to withstand pressure of twenty pounds per square inch plus or minus two pounds per square inch. The potting compound preferably is filled to establish a flush surface with respect to the edge of the L-shaped housing 12, thereby covering and enclosing the lead wires 47 with a minimum thickness of potting compound approximating 100 mil.

The purpose of the transmitter/transducer 24 is to generate ultrasonic sound waves for detection by the receiver/transponder 36. The reduction of standing waves, and/or standing wave signals caused by the reflection/refraction of the ultrasonic sound waves within the L-shaped housing 12, is of primary importance. The optimization for reduction of the signal-to-noise ratio and improvement of the accuracy and performance of the gas saving device 10 is highly desirable.

The transmitter/transducer 24 is preferably able to function and produce a stable output of ultrasonic sound waves over a temperature range of 10° to 45° C. A stable output of ultrasonic sound waves is required in order to provide an operating frequency for the transmitter/transducer 24, and for receipt by the receiver/transponder 36, such that the sound-wave delay measurement must fall within one period of the oscillator frequency. The preferred operational frequency for the transmitter/transducer 24 is 40 khz.

The transmitter/transducer 24 is preferably selected to provide sound delays within the transducer chamber such that the pulse width determined by the electronic circuits remains within a twenty-five micro second window of the oscillator. Preferably the pulse width for the ultrasonic signals continues within one to twenty-four micro seconds over the full temperature and concentration ranges for the gas detection device 10. The pulse width for the ultrasonic signals may be controlled by selecting the correct polarity of the transmitter/transducer 24 and receiver/transponder 36 elements. It should be noted that the total sound delay through the transducer chamber is greater than the actual pulse width measured. The following formula is used for determination of the pulse width for the ultrasonic signals; the "pulse width" equals the "total delay" through the transducer chamber minus the number of oscillation cycles multiplied by the oscillation period. The transmitter/transducer 24 is preferably selected for its temperature stability and its operating frequency. The temperature stability is required for the transmitter/transducer 24 characteristics to remain stable and resist change over the operating temperature range of the device. The operating frequency is preferably selected for the availability of the gas-sensor device 10 and the pulse width range at the indicated frequency.

The preferred distance between the transmitter/transducer 24 and the receiver/transponder 36 approximates $0.850 \pm 0.005$ inches. The transmitter/transducer 24 in the preferred embodiment is a Panasonic P/N EFROSB 4$\phi$K65 unit. In the preferred embodiment, the diode 26 is preferably a IN4148 unit as available from National SemiConductor, Inc.

In general, the gas outflow end cap assembly 28 includes a sonic baffle 30 and a gas outlet port 32. The gas outlet port 32 is preferably formed of the same polycarbonate or plastic material as the L-shaped housing 12 and the transmitter end cap 68.

The gas outflow end cap assembly 28 in general includes a circular base 76 having a centrally-positioned aperture 78 therethrough, and a cylindrically-shaped barbed extension 80 extending outward from the circular base 76. The cylindrical-shaped barb extension 80 is preferably aligned to the centrally-positioned aperture 78. The diameter dimension for the centrally-positioned aperture 78 and the cylindrically-shaped barbed extension 80, is preferably the same as the diameter dimension for central aperture 58 of the gas inlet port 20. The diameter dimension for the circular base 76 is preferably equal to the diameter dimension for the first channel surface 48. The circular base 76 is preferably adapted for flush and airtight engagement to the first channel surface 48. The purpose of the circular base 76 is to seal the second open gas outflow end 16 defining a gas flow course from the gas inlet port 20 to the gas outlet port 32. Another purpose of the circular base 76 is to fixedly position the sonic baffle 30 within the second open outflow end 16.

The sonic baffle 30 preferably includes a collar 82 which is affixed to the circular base 76 proximal to its circumference. The sonic baffle 30 is preferably conical in shape, and includes a plurality of baffle slots 84 which extend longitudinally through the conical portion. The sonic baffle 30 extends outwardly from the circular base 76 where the tip of the conical portion is positioned centrally within the interior of the second open gas outflow end 16 facing the receiver/transponder 36. The collar 82 is preferably positioned in flush contact with the ridge established between the first channel surface 48 and the second interior surface 50, which functions as a stop, limiting the penetrating engagement of the gas outflow end cap assembly 28 within the second open outflow end 16. It should be noted that the sonic baffle 30 completely traverses the interior of the L-shaped housing 12 proximal to the second open gas outflow end 16.

The sonic baffle 30 is preferably formed of injected molded plastic and functions to dampen and reduce reflected and/or refracted ultrasonic sound waves within the L-shaped housing 12. Sonic baffle 30 functions to significantly reduce the standing waves within the L-shaped housing 12. The minimization of standing waves significantly enhances the performance of the gas-sensor device 10 by improving the signal-to-noise ratio and elevating of the performance of the receiver/transponder 36. The baffle slots 84 function to permit passage of air into the rear interior of the sonic baffle 30.

It should be noted that a binary gas flow course is established within the interior of the L-shaped housing 12, between the gas inlet port 20 and the gas outlet port 32. Initially, a binary gas source is attached to the gas inlet port 20. The binary gas source preferably permits access of gas within the gas-sensor device 10 at a rate of zero to five liters per minute. The binary gas initially enters the transducer chamber proximal to the transmitter/transducer 24. The binary gas then flows toward the receiver/transponder 36 as indicated by arrow 5. The binary gas then follows the L-shaped housing 12 toward the sonic baffle 30 and the gas outlet port 32 as indicated by arrow 6. The binary gas then exits the L-shaped housing 12, via the gas outlet port 32, as indicated by arrow 7. The interior of the L-shaped housing 12 is preferably sealed for limiting access of the binary gas air-flow course between the gas inlet port 20 and the gas outlet port 32. A desired level of pressure within the gas-sensor device 10 is thereby sustained.

The second open gas outflow end 16 is preferably sealed by the application and drying of potting compound which forms a good seal. The seal of the gas outflow end cap assembly 28 to the second open gas outflow end 16 is preferably of sufficient strength to withstand internal pressure approximating twenty pounds per square inch. Following curing of the potting compound, for a period approximating 24 hours, the seal of the second open gas outflow end 16 is preferable to withstand a pressure of twenty pounds per square inch, plus or minus two pounds per square inch. A volume of potting compound is preferably filled into the second open gas outflow end 16 in order to establish a flush surface with respect to the edge of the L-shaped housing 12, having a minimum thickness approximating 100 mil.

In general, the receiver assembly 34 includes a receiver/transponder 36 mounted to a receiver base 85, an electrical connection 86, an electrical connection 88, and a receiver end cap 90. The receiver end cap 90 is preferably formed of the same plastic material as the L-shaped housing 12. The receiver end cap 90 is preferably cylindrical in shape having a diameter dimension adapted for flush and sealed engagement to the second ridge surface 54 of the junction open receiver end 18. The width dimension of the receiver end cap 90 is preferably equal to the width dimension of the second ridge surface 54. The receiver end cap 90 includes a pair of apertures 92 which are adapted for alignment to the engagement slots 46a of the first ridge surface 52. The apertures 92 provide for the convenient electrical connection of lead wires 49 to the electrical connection 86 and the electrical connection 88.

The purpose of the receiver end cap 90 is to seal the junction open receiver end 18 and centrally position the receiver/transponder 36 within the interior of the L-shaped housing 12. Another purpose of the receiver end cap 90 is to position the receiver/transponder 36 at a fixed location within the transducer chamber, such that a defined calculated distance dimension exists between the transmitter/transducer 24 and the receiver/transponder 36.

The receiver/transponder 36 is preferably mounted to a receiver base 85 which is cylindrical in shape and is formed of the same plastic material as the receiver end cap 90. The electrical connection 86 and the electrical connection 88 preferably pass through the receiver base 85 for ultimate electrical connection to the lead wires 49. The electrical connection 86 and the electrical connection 88 pass through the respective pair of apertures 92 of the receiver end cap 90. It should also be noted that the receiver base 85 is preferably affixed to the receiver end cap 90 and is positioned for flush engagement thereto. It should also be noted that the lead wires 49 are positioned for electrical connection to the electrical connection 86 and the electrical connection 88.

The receiver end cap 90, the electrical connection 86, and the electrical connection 88 are preferably sealed within the junction open receiver end 18 by potting compound. It should be noted that the pair of apertures 92 of the receiver end cap 90 are preferably restricted or plugged following engagement to the electrical ground connection 86 and electrical output connection 88 in order to facilitate sealing of the junction open receiver end 18. Following the curing of the potting compound, for a period approximating twenty-four hours, the sealing of the receiving end cap 90, within the junction open receiver end 18, should occur where the seal is able to withstand a pressure of twenty pounds per square inch, plus or minus two pounds per square inch. A volume of potting compound preferably is into the junction open receiver end 18 to establish a flush surface with respect to the edge of the L-shaped housing 12, thereby covering and enclosing the lead wires 49 with a minimum thickness of potting compound approximating 100 mil.

Figure 4:
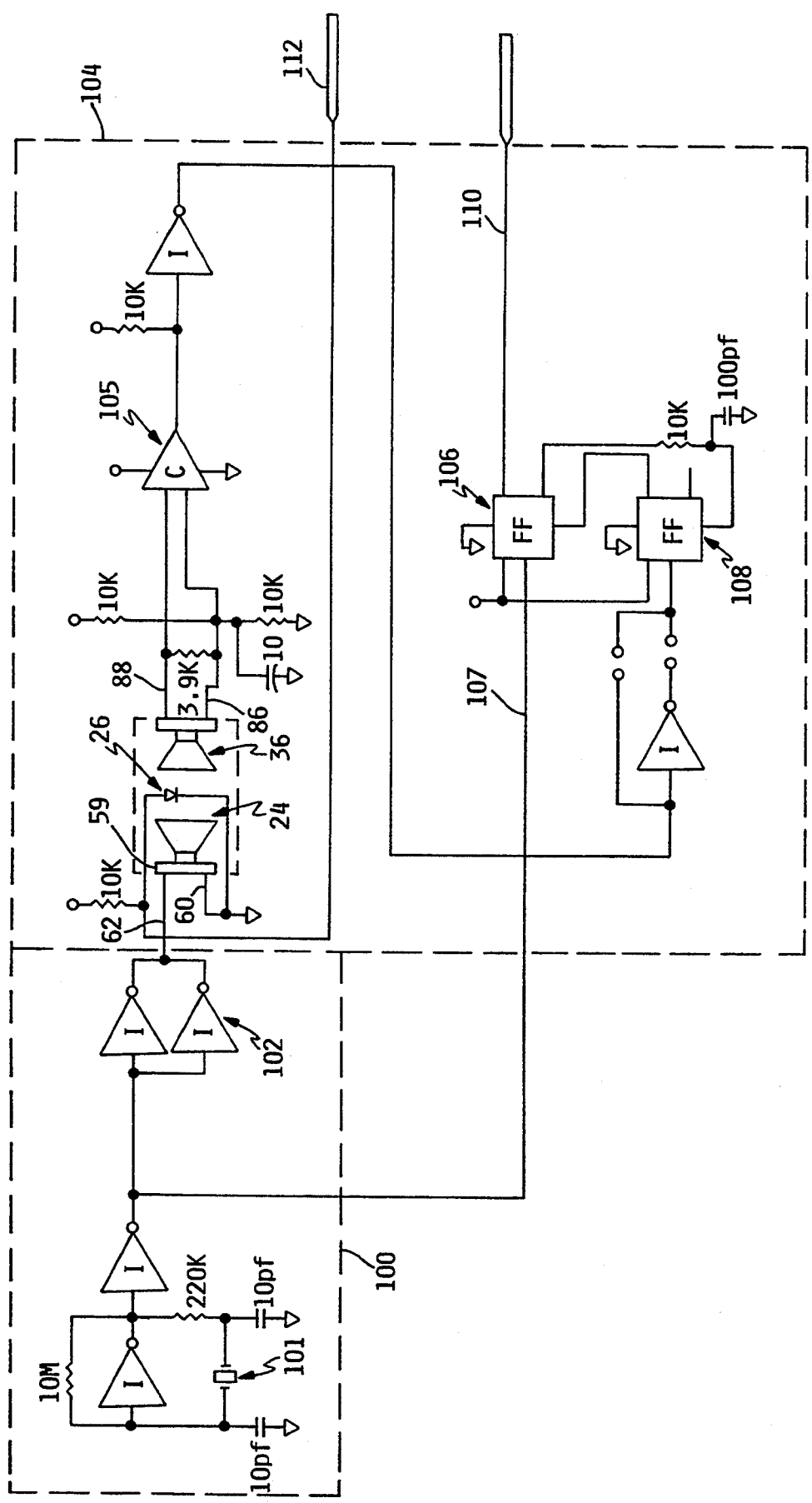
FIG. 4 is a circuit diagram showing the transmitter and receiver circuits.

Referring next to FIG. 4, a circuit diagram illustrating the transmitter and receiver circuits is illustrated. An oscillator/driver circuit 100 generates a continuous sequence of pulses at a frequency determined by crystal oscillator 101. Crystal oscillator 101 is preferably selected to provide a 40 khz signal. The oscillator frequency signal is shaped and amplified by drivers 102, and applied to transmitter 24 via input connection 62. Input connection 60 is connected to ground potential. Transmitter 24 forms a part of the sensor and signal condition circuits 104. Transmitter 24 generates an acoustical signal which is received by receiver 36, and converted into an electrical signal applied across electrical connections 86 and 88. These signals are connected to a comparator 105 which generates an output signal whenever the input signal exceeds a predetermined value. The output from comparator 105 is applied via inverter circuits to a flip-flop circuit 108. Flip-flop circuit 106 receives the initial oscillator pulse signal via line 107, indicative of the time at which the initial signal was generated. The signal on line 107 causes flip-flop circuit 106 to become set, thereby generating a signal on line 110; the signal from flip-flop circuit 108 causes flip-flop 106 to reset, thereby removing the signal on line 110. Therefore, the signal on line 10 is present during the time interval beginning with a generation of the oscillator signal and ending with the receipt of the acoustical signal by receiver 36. Temperature diode 26 generates a voltage level on output line 112, which voltage is representative of the temperature within housing 12.

Figure 5:
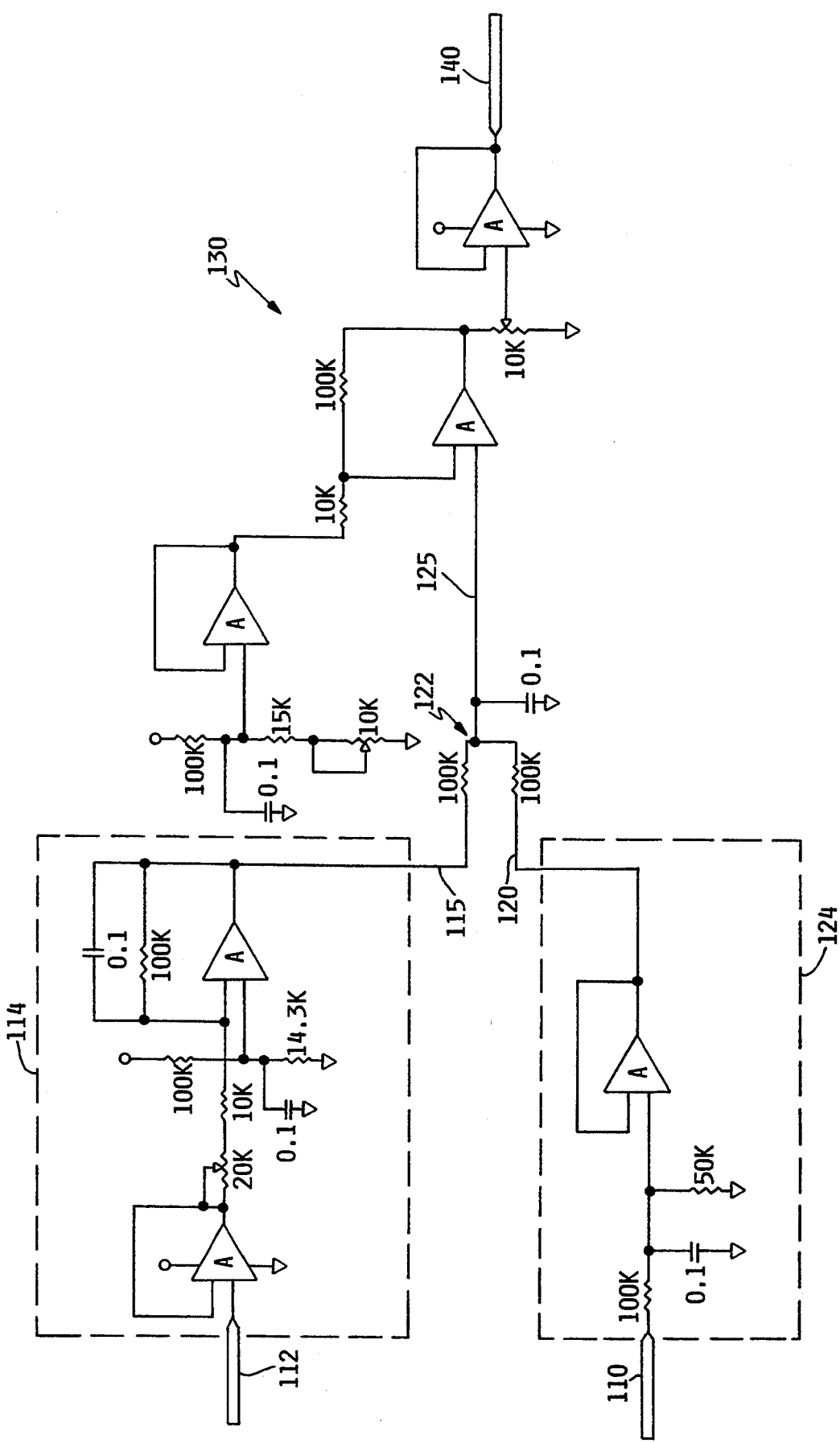
FIG. 5 is a circuit diagram showing the signal processing circuits.

Referring to FIG. 5, the temperature signal on line 112 is coupled into temperature compensation circuit 114. This signal is compared against a reference value and is applied to a summing circuit 122 via line 115. The sensor circuit output signal on line 110 is applied to a pulse width/voltage converter circuit 124, which integrates the pulse signal input to develop an output voltage on line 120 which is the function of the time of the input pulse. The signals on lines 115 and 120 are applied to summer circuit 122, and the sum of these signals is applied via line 125 to the calibration and output circuit 130. The calibration and output circuit 130 provides potentiometer adjustments for calibrating the ambient temperature value and the maximum voltage swing for the output signal. This circuit is adjusted so as to provide an analog output voltage on line 140 which is directly representative of the oxygen content of the gas flowing through gas-sensor device 10.

The circuit components utilized in the diagrams of FIGS. 4 and 5 are commercially available components, which may be obtained from a number of manufacturers under well-known type designations. For example, the amplifiers A are preferably Type LM358 or Type LM324 circuits; the inverters I are preferably Type 4049 circuits; the flip-flop circuits are preferably Type 4013 circuits, available from various manufacturers such as Motorola.

The purpose of the receiver/transponder 36 is to detect ultrasonic sound waves as produced by the transmitter/transducer 22. The receiver/transponder 36 is preferably positioned parallel to the junction open receiver end 18, which angularly offsets the position of the receiver/transponder 36 with respect to the transmitter/transducer 24 by an angle of approximately 45°. The angularly offset positioning of the receiver/transponder 36 with respect to the transmitter/transducer 24 reduces reflection of ultrasonic sound waves back toward the transmitter/transducer 24, thereby significantly reducing standing waves. It is expected that ultrasonic waves reflecting off the receiver/transponder 36 emanate toward the sonic baffle 30, as opposed to return to the transmitter/transducer 24. It should be noted that the receiver/transponder 36 is centrally positioned within the interior of the L-shaped housing 12 proximal to the junction open receiver end 18 and is unobstructively aligned to the transmitter/transducer 24.

The receiver/transponder 36 operates on the frequency of 40 khz for receipt of signals as generated by the transmitter/transducer 24. The spacing between the transmitter/transducer 24 and the receiver/transponder 36 is selected to provide sound delays in the transducer chamber such that the pulse width determined by the electronic circuitry remains within a twenty-five micro second window of the oscillator. The pulse width for the signal preferably continues within one to twenty-four micro seconds over the full temperature and concentration operational ranges for the gas-sensor device 10. The pulse width can be controlled also by selecting the correct polarity of the transmitter/transducer 24 or receiver/transponder 36 elements. It should be noted that the total sound delay through the transducer chamber is greater than the actual pulse width measured. The receiver/transponder 36 is preferably selected for its temperature stability within the noted operating frequency. Temperature stability is required so that the receiver/transponder 36 characteristics do not change over the operating temperature ranges for the device. The receiver/transponder 36 is preferably located 0.85 inches from the transmitter/transducer 24. The mounting of the receiver/transponder 36 at a 45° degree angle from the center line of the transmitter/transducer 24 reduces the reflection effects of ultrasonic waves back into emanating sounds waves from the transmitter/transducer 24. It is also required that the receiver/transponder 36 include a reasonably constant output amplitude over the full concentration ranges of gas to be detected. If the receiver/transponder 36 amplitude is not constant, the rise time of the output signal will have an effect on the measured output. The spacing of the receiver/transponder 36 from a transmitter/transducer 24 must be selected so that the pulse width value falls within twenty-five micro seconds. Therefore, this spacing should approximate 0.850±0.005 inches. The actual sound delay between the transmitter/transducer 24 and the receiver/transponder 36 is between 50 to 75 micro seconds. During the generation of a continuous ultrasonic sound wave through the transducer chamber, 50 micro seconds are subtracted off the total time by starting the pulse width measurement with the oscillator signal. During implementation of a pulsed ultrasonic sound waves through the transducer chamber, 50 micro seconds are subtracted by delaying the start pulse by an appropriate amount. Therefore, the spacing would be identical for both excitation methods.

The mounting of the receiver/transponder 36 the end of a straight chamber operates efficiently for pulsed mode operations. Standing sound waves are minimized due to the dying out of the ultrasonic sound waves between each burst of sound pulses. During use of a continuous ultrasonic sound-wave signal, the use of a straight tube causes the ultrasonic sound waves to bounce off the receiver/transponder 36 back into the oncoming ultrasonic waves, which extenuates the incoming signals at different rates over the concentration range. This phenomena causes the output error to be larger than desired. Therefore, the L-shaped housing 12 is preferred when a continuous ultrasonic sound wave is generated. In this embodiment, the ultrasonic sound waves travel down the L-shaped housing 12 where they are reflected off the receiver/transponder 36 down into the second open gas outflow end 16, which includes the sonic baffle 30. The sonic baffle 30 functions to dampen the signal as the ultrasonic sound waves contact the sonic baffle 30 and the sound buffer means 74. The receiver/transponder 36 is preferably a Panasonic EFRRSB 4φK65 unit.

The sound buffer 74 is preferably positioned proximal to the interior walls of the L-shaped housing 12 within the first open transmitter end 14 and the second open gas outflow end 16. The sound buffer 74 preferably reduces reflective/refracted ultrasonic sound waves within the L-shaped housing 12. The sound buffer 74 is preferably formed of a fabric material, and in the preferred embodiment is comprised of wool felt. Alternatively, any preferred material may be used as the sound buffer 74, including but not limited to the use of cotton, paper, synthetic fibers, and/or foam sound insulating material, provided that the essential functions, features, and attributes described herein are not sacrificed. It should be noted that the sound buffer 74 completely covers the interior of the L-shaped housing 12 including the transducer chamber, without gaps especially along mating seams. The edges of the sound buffer 74 are preferably cut to flushly cover all interior surfaces of the L-shaped housing without overlap of material.

The sound buffer 74 preferably functions to reduce the reflection/refraction of ultrasonic sound waves as generated by the transmitter/transducer 24. The reduction of reflected/refracted ultrasonic sound waves minimizes standing waves, which in turn minimizes background noise, thereby improving the signal-to-noise ratio and performance of the gas-sensor device 10. A more accurate determination of the concentration of oxygen within a binary gas sample is therefore available.

The primary function of the sound buffer 74 is to attenuate the reflection of ultrasonic sound waves off of the internal sidewalls of the L-shaped housing 12. The sound buffer 74 is preferably sufficiently dense to keep ultrasonic sound waves from traversing the fabric material and reflecting back through the material into the interior of the L-shaped housing 12. The material selected for the sound buffer 74 may, however, not be so dense as to cause that ultrasonic sound waves to reflect off the sound buffer 74, thereby escalating the volume and amount of standing waves and background noise within the interior of the L-shaped housing 12. It should be noted that many acoustical foams do not include a sufficient density to attenuate ultrasonic sound waves before reflecting off of the sidewalls of the interior of the L-shaped housing 12. These acoustical foams attenuate sound waves below 5 khz. In addition to the reduction of standing waves within the interior of the L-shaped housing 12, the sound buffer 74 preferably reduces the turbulence between the transmitter/transducer 24 and the receiver/transponder 36.

The sound buffer, in the form of wool felt, 74 may be obtained from the manufacture of Armstrong/Kover Kwick Inc., part no. KK5016 which has 1/16 inch thickness dimension and a density/weight of one pound per square inch.

During operation of the gas-sensor device 10, the temperature of the binary gas is required to be measured via the diode 26 in order to compensate the output reading for an accurate determination of the concentration of oxygen within the gas sample. As the temperature of the binary gas increases, the ultrasonic sound waves generated within the L-shaped housing 12 travel through the binary gas at a faster rate due to the molecules of the gas moving at an increased rate due to the higher temperature. The object of the gas-sensor device 10 is to calculate the concentration of oxygen within the gas sample. The humidity of the binary gas sample effects the ultrasonic sound-wave delay between the transmitter/transducer 24 and the receiver/transponder 36. If the gas-sensor device 10 is to be used as a portion of an oxygen concentrator apparatus, then the humidity parameter factor may be ignored. In addition, the pressure level of the binary gas sample may effect the performance of the gas-sensor device 10. Again, if an oxygen concentrator device is used, the pressure is typically regulated at a constant five pounds per square inch. Thus, the pressure parameter may also be ignored. Generally, the ultrasonic sound-wave equation generated by a gas-sensor device is nonlinear over distance; however, at the distance which the ultrasonic sound waves travel within the transducer chamber the ultrasonic sound-wave equation may be considered as linear for calculation purposes. If continuous ultrasonic sound-wave operation is required for the gas-sensor device 10, an L-shaped housing 12 should be used to keep the ultrasonic sound waves from being reflected back into the oncoming ultrasonic sound waves as generated by the transmitter/transducer 24. If the gas-sensor device 10 is to be used in determinations of oxygen concentration below forty percent, the pulsed method for generation of ultrasonic sound waves is preferred above a continuous ultrasonic sound-wave generation device.

It should be noted that during use of the gas-sensor device 10, the gas inlet port 20 and gas outlet port 32 are located such that the binary gas sample must cross the path of the ultrasonic sound waves generated within the transducer chamber. The gas inlet port 20 is located proximal to and in front of the transmitter/transducer 24. The gas outlet port 32 is positioned in the gas outflow end cap assembly 28 which is at the opposite end of the L-shaped housing 12 from the transmitter/transducer 24. The gas flow path is generally shown by arrows 5, 6 and 7 in FIG. 2.

The present invention may be embodied in other specific forms without departing from the spirit or essential attributes thereof; therefore, the illustrated embodiment should be considered in all respects as illustrative and not restrictive, reference being made to the appended claims rather than to the foregoing description to indicate the scope of the invention.

What is claimed is:

1. A gas-sensor device for detection of the presence and concentration of a gas, said gas-sensor device comprising:
    (a) an L-shaped housing having a first transmitter end, a second gas outflow end, a junction receiver end, and a gas inlet port through said L-shaped housing proximal to said first transmitter end, said gas inlet port permitting flow-through access of said gas to be detected;
    (b) a transmitter assembly having a transmitter/transducer and a temperature sensor positioned in said first transmitter end, said transmitter/transducer having means for generating sound waves for passing through said gas within said L-shaped housing;
    (c) a gas outflow end cap assembly having a sonic baffle and a gas outlet port positioned in said second gas outflow end, said sonic baffle having means for reducing reflection of said sound waves within the said L-shaped housing;
    (d) a receiver assembly having a receiver/transponder for receipt of said sound waves positioned in said junction receiver end; and
    (e) a sound buffer means for reduction of reflected sound waves, said sound buffer means engaged to said L-shaped housing, said first transmitter end, said second gas outflow end, and to said receiver assembly.

2. The gas-sensor device according to claim 1, wherein said L-shaped housing is tubular in shape.

3. The gas-sensor device according to claim 1, wherein said L-shaped housing has a first grooved surface proximal to said first transmitter end.

4. The gas-sensor device according to claim 3, wherein said L-shaped housing has a second grooved surface of smaller diameter than said first grooved surface, said second grooved surface being positioned proximal to said first grooved surface within said first transmitter end of said L-shaped housing.

5. The gas-sensor device according to claim 4, wherein said first transmitter end has a first interior surface of smaller diameter than said second grooved surface, said first interior surface being positioned proximal to said second grooved surface within said first transmitter end of said L-shaped housing.

6. The gas-sensor device according to claim 5, wherein said second gas outflow end has a first channel surface.

7. The gas-sensor device according to claim 6, wherein said second gas outflow end has a second interior surface of smaller diameter than said first channel surface, said second interior surface being positioned proximal to said first channel surface within said second gas outflow end of said L-shaped housing.

8. The gas-sensor device according to claim 1, wherein said junction receiver end has a stop ledge.

9. The gas-sensor device according to claim 1, wherein said transmitter assembly has a transmitter end cap, and input electrical connections affixed to said transmitter/transducer which pass through said transmitter end cap.

10. The gas-sensor device according to claim 9, wherein said temperature sensor further comprises a diode having anode and cathode electrical connections which pass through said transmitter end cap.

11. The gas-sensor device according to claim 1, wherein said temperature sensor is angularly offset with respect to said L-shaped housing and is positioned adjacent to said sound buffer means.

12. The gas-sensor device according to claim 1, wherein said temperature sensor is responsive to the temperature within said L-shaped housing.

13. The gas-sensor device according to claim 1, wherein said transmitter/transducer includes means for generating ultrasonic sound waves.

14. The gas-sensor device according to claim 1, wherein said sonic baffle is conical in shape extending within said L-shaped housing toward said junction receiver end.

15. The gas-sensor device according to claim 1, wherein said gas outlet port has a circular base having a centrally-positioned aperture therethrough and a cylindrical-shaped barbed extension aligned to said aperture.

16. A gas-sensor device according to claim 15, wherein said sonic baffle is affixed to, and extends inwardly from, said circular base of said gas outlet port.

17. The gas-sensor device according to claim 1, wherein said sonic baffle has a plurality of longitudinal slots.

18. The gas-sensor device according to claim 1, wherein said receiver assembly has a receiver end cap, and output electrical connections affixed to said receiver/transponder which traverse said receiver end cap.

19. The gas-sensor device according to claim 1, wherein said receiver assembly is angularly offset with respect to said L-shaped housing.

20. The gas-sensor device according to claim 19, wherein said receiver/transponder is angularly offset with respect to said L-shaped housing at an angle of 45°.

21. The gas-sensor device according to claim 1, wherein said transmitter/transducer and said receiver/transponder are aligned to one another within said L-shaped housing.

22. The gas-sensor device according to claim 1, wherein said sound buffer means comprises at least one felt insert.

23. The gas-sensor device according to claim 7, wherein said sound buffer means engages said first interior surface of said first transmitter end and said second interior surface of said second gas outflow end.

24. A gas-sensor device for detection of the presence and concentration of a gas, said gas-sensor device comprising:
    (a) an L-shaped housing having a first transmitter end, a second gas outflow end, a junction receiver end, and a gas inlet port through said L-shaped housing proximal to said first transmitter end, said gas inlet port permitting flow-through access of said gas to be detected;

(b) a transmitter assembly having a transmitter/transducer and a temperature sensor positioned in said first transmitter end, said transmitter/transducer having means for generating sound waves for passing through said gas within said L-shaped housing;

(c) a gas outflow end cap assembly having a sonic baffle and a gas outlet port positioned in said second gas outflow end, said sonic baffle having means for reducing reflection of said sound waves within said L-shaped housing;

(d) a receiver assembly having a receiver/transponder means for receipt of said sound waves, positioned in said junction receiver end; and (e) a fabric insert for reduction of reflected sound waves, said fabric insert being positioned within said L-shaped housing and being further engaged to said first transmitter end, said transmitter assembly, said second gas outflow end, said gas outflow end cap assembly, and to said receiver assembly.

25. The gas-sensor device according to claim 24, wherein said L-shaped housing is tubular in shape.

26. The gas-sensor device according to claim 24, wherein said L-shaped housing has a first grooved surface proximal to said first transmitter end.

27. The gas-sensor device according to claim 26, wherein said L-shaped housing has a second grooved surface of smaller diameter than said first grooved surface, said second grooved surface being positioned proximal to said first grooved surface within said first transmitter end of said L-shaped housing.

28. The gas-sensor device according to claim 27, wherein said first transmitter end has a first interior surface of smaller diameter than said second grooved surface, said first interior surface being positioned proximal to said second grooved surface within said first transmitter end of said L-shaped housing.

29. The gas-sensor device according to claim 28, wherein said second gas outflow end has a first channel surface.

30. The gas-sensor device according to claim 29, wherein said second gas outflow end has a second interior surface of smaller diameter than said first channel surface, said second interior surface being positioned proximal to said first channel surface within said second gas outflow end of said L-shaped housing.

31. The gas-sensor device according to claim 24, wherein said junction receiver end has a stop ledge.

32. The gas-sensor device according to claim 24, wherein said transmitter assembly has a transmitter end cap, and input electrical connections affixed to said transmitter/transducer which pass through said transmitter end cap.

33. The gas-sensor device according to claim 32, wherein said temperature sensor further comprises a diode having anode and cathode electrical connections which pass through said transmitter end cap.

34. The gas-sensor device according to claim 24, wherein said temperature sensor is angularly offset with respect to said L-shaped housing and is positioned adjacent to said sound buffer means.

35. The gas-sensor device according to claim 24, wherein said temperature sensor includes means for measuring the temperature within said L-shaped housing.

36. The gas-sensor device according to claim 24, wherein said transmitter/transducer includes means for generating ultrasonic sound waves.

37. The gas-sensor device according to claim 36, wherein said sonic baffle is conical in shape extending within said L-shaped housing toward said junction receiver end.

38. The gas-sensor device according to claim 24, wherein said gas outlet port has a circular base having a centrally-positioned aperture therethrough and a cylindrical-shaped barbed extension aligned to said aperture.

39. A gas-sensor device according to claim 38, wherein said sonic baffle is affixed to, and extends inwardly from, said circular base of said gas outlet port.

40. The gas-sensor device according to claim 24, wherein said sonic baffle has a plurality of longitudinal slots.

41. The gas-sensor device according to claim 24, wherein said receiver assembly has a receiver end cap, and output electrical connections affixed to said receiver/transponder which traverse said receiver end cap.

42. The gas-sensor device according to claim 24, wherein said receiver assembly is angularly offset with respect to said L-shaped housing.

43. The gas-sensor device according to claim 42, wherein said receiver/transponder is angularly offset with respect to said L-shaped housing at an angle of 45°.

44. The gas-sensor device according to claim 24, wherein said transmitter/transducer and said receiver/transponder are aligned to one another within said L-shaped housing.

45. The gas-sensor device according to claim 24, wherein said fabric insert is comprised of felt.

46. The gas-sensor device according to claim 30, wherein said fabric insert is engaged to said first interior surface of said first transmitter end and said second interior surface of said second gas outflow end.

* * * * *